(12) United States Patent
Borgmeier et al.

(10) Patent No.: US 7,214,822 B2
(45) Date of Patent: *May 8, 2007

(54) CATALYST COMPRISING A SUPPORT AND A CATALYTICALLY ACTIVE OXIDE MATERIAL APPLIED TO THE SURFACE OF THE SUBSTRATE

(75) Inventors: Frieder Borgmeier, Mannheim (DE); Andreas Tenten, Maikammer (DE); Hartmut Hibst, Schriesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/228,285

(22) Filed: Sep. 19, 2005

(65) Prior Publication Data

US 2006/0074258 A1    Apr. 6, 2006

Related U.S. Application Data

(62) Division of application No. 10/399,039, filed as application No. PCT/EP01/11909 on Oct. 16, 2001.

(30) Foreign Application Priority Data

Oct. 17, 2000    (DE)  ............................... 100 51 419

(51) Int. Cl.
     *B01J 23/00*    (2006.01)
(52) U.S. Cl. ...................... 562/549; 502/311; 502/321; 502/308; 502/309; 502/312; 502/322; 502/514; 502/527.14; 502/527.15; 502/527.16; 502/527.17
(58) Field of Classification Search ................ 502/312, 502/311, 321, 308, 309, 322, 514, 527.14, 502/527.15, 527.16, 527.17; 562/549
See application file for complete search history.

(56) References Cited

U.S. PATENT DOCUMENTS

| 4,524,236 | A | 6/1985 | McCain |
| 4,565,658 | A | 1/1986 | Ebner |
| 5,281,745 | A | 1/1994 | Ushikubo et al. |
| 5,380,933 | A | 1/1995 | Ushikubo et al. |
| 5,677,261 | A | 10/1997 | Tenten et al. |
| 5,910,608 | A | 6/1999 | Tenten et al. |
| 6,043,185 | A | 3/2000 | Cassidy et al. |
| 6,063,728 | A | 5/2000 | Hinago et al. |
| 6,143,690 | A | 11/2000 | Komada et al. |
| 6,143,916 | A | 11/2000 | Hinago et al. |
| 6,169,214 | B1 | 1/2001 | Tenten et al. |
| 6,858,754 | B2 | 2/2005 | Borgmeier |
| 6,867,328 | B2 | 3/2005 | Borgmeier et al. |
| 2003/0187298 | A1 | 10/2003 | Borgmeier et al. |
| 2003/0187299 | A1 | 10/2003 | Machhammer et al. |
| 2004/0138500 | A1 | 7/2004 | Borgmeier |

FOREIGN PATENT DOCUMENTS

| DE | 44 42 346 | 5/1996 |
| DE | 198 35 247 | 2/1999 |
| DE | 100 29 338 | 1/2002 |
| DE | 100 46 672 | 3/2002 |
| EP | 0 529 853 | 3/1993 |
| EP | 0 608 838 | 8/1994 |
| EP | 767164 | 4/1997 |
| EP | 0 895 809 | 2/1999 |
| EP | 962253 | 12/1999 |
| EP | 1 090 684 | 4/2001 |
| JP | 07-232071 | 9/1995 |
| JP | 10-036311 | 2/1998 |
| JP | 10-057813 | 3/1998 |
| JP | 11-169716 | 6/1999 |
| JP | 2000-037623 | 2/2000 |
| WO | 00/29106 | 5/2000 |

OTHER PUBLICATIONS

Robert K. Grasselli, Catalysis Today, vol. 49, pp. 141-153, 1999.
Applied Catalysis A: General 194-195, pp. 479-485, 2000.
Manhua Lin et al., "Reaction Intermediates in the Selective Oxidation of Propane Over a Mixed Metal Oxide Catalyst", Proceedings ISO '99, Rimini (Italy), Sep. 10-11, 1999, G. Centi and S. Perathoner Ed., SCi Pub., pp. 143-144.
G. Centi et al., "In situ DRIFT study of the reactivity and reaction mechanism of catalysts based on iron-molybdenum oxides encapsulated in boralite for the selective oxidation of alkylaromatics", Catalysis Today, vol. 61, 2000, pp. 211-221.
Manhua Lin et al., "Reaction pathways in the selective oxidation of propane over a mixed metal oxide catalyst", Catalysis Today, vol. 61, 2000, pp. 223-229.
Manhua LIN, et al., "Reaction Pathways in the Selective Oxidation of Propane Over a Mixed Metal Oxide Catalyst," Catalysis Today, 61, 2000, pp. 223-229.

*Primary Examiner*—Stuart L. Hendrickson
*Assistant Examiner*—Paul Wartalowicz
(74) *Attorney, Agent, or Firm*—Oblon, Spivak, McClelland, Maier & Neustadt, P.C.

(57) ABSTRACT

A coated catalyst whose coating of active composition is a multimetal oxide comprising the elements Mo, V and Te and/or Sb can be used for the gas-phase catalytic oxidation of propane to acrylic acid.

15 Claims, 2 Drawing Sheets

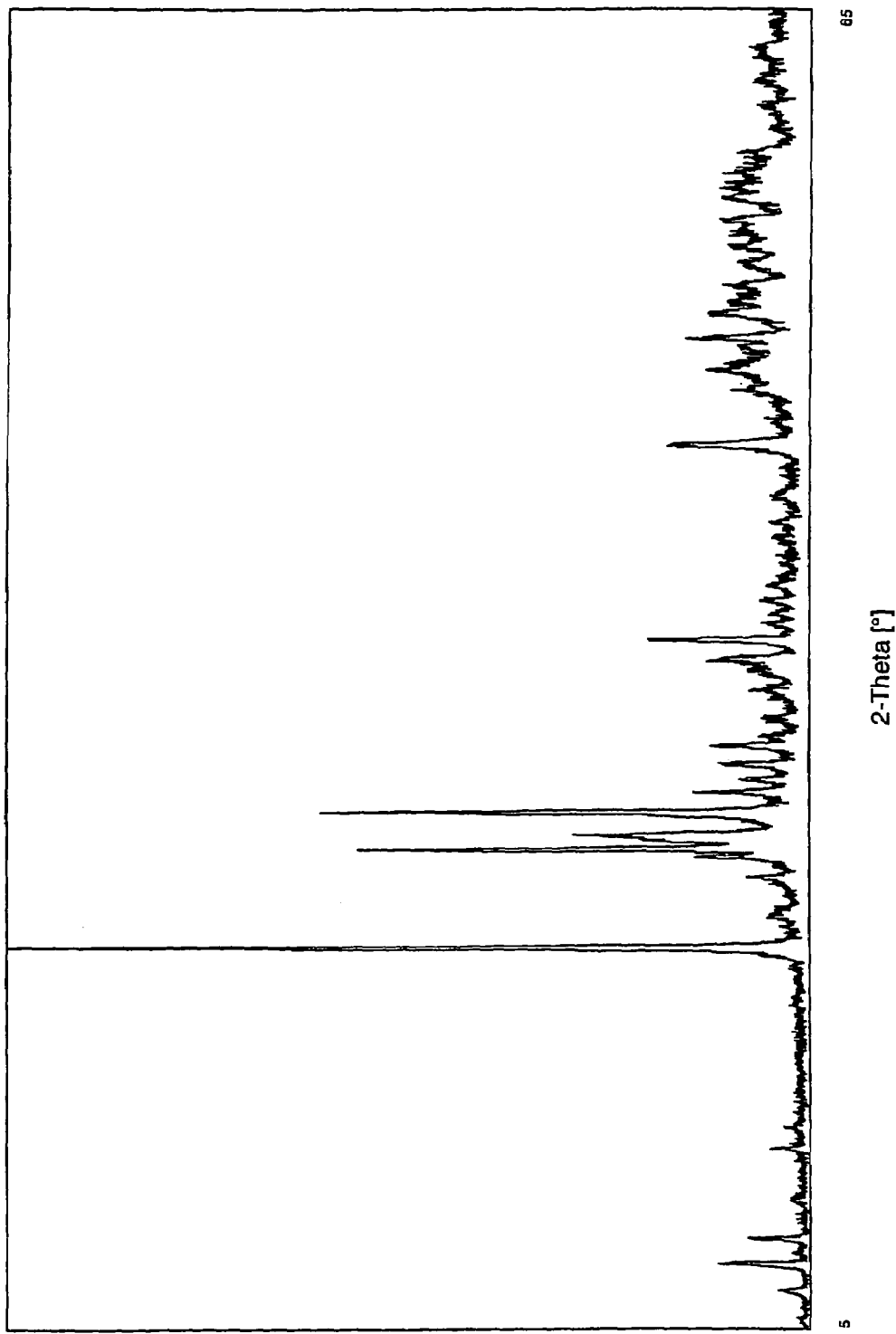

CATALYST COMPRISING A SUPPORT AND A CATALYTICALLY ACTIVE OXIDE MATERIAL APPLIED TO THE SURFACE OF THE SUBSTRATE

CROSS-REFERENCE TO RELATED APPLICATIONS

This application is a divisional of U.S. application Ser. No. 10/399,039, filed on Apr. 17, 2004, which is a National Stage (371) of PCT/EP01/11909, filed on Oct. 16, 2001, which claims priority to DE 10051419.7, filed on Oct. 17, 2000.

BACKGROUND OF THE INVENTION

1. Field of the Invention

The present invention relates to a catalyst comprising a support body and a catalytically active oxide composition of the formula I $$Mo_1V_bM_c^1M_d^2O_n \qquad (I),$$

where
 $M^1$=Te and/or Sb,
 $M^2$=at least one element selected from the group consisting of Nb, Ta, W, Ti, Al, Zr, Cr, Mn, Ga, Fe, Ru, Co, Rh, Ni, Pd, Pt, Bi, B and Ce,
 b=0.01 to 1,
 c=0.01 to 1,
 d=0.01 to 1 and
 n=a number required to achieve electrical neutrality and determined by the valence and abundance of the elements other than oxygen in (I), applied to the surface of the support body.

The present invention also relates to the use of the above-described coated catalysts as catalysts for the heterogeneously catalyzed gas-phase oxidation of propane to acrylic acid.

2. Discussion of the Background

Multimetal oxide compositions having a stoichiometry corresponding to the formula I are known (cf., for example, EP-A 608838, EP-A 529853, JP-A 7-232071, JP-A 10-57813, JP-A 2000-37623, JP-A 10-36311, Proceedings ISO'99, Rimini (Italy), Sep. 10–11, 1999, G. Centi and S. Perathoner Ed., SCI Pub. 1999, EP-A 767164, Catalysis Today 49(1999), pp. 141–153, EP-A 962253, Applied Catalysis A: General 194 to 195 (2000), pp. 479 to 485, JP-A 11/169716, EP-A 895809 and DE-A 19835247) and have also been proposed in the earlier patent applications DE-A 10029338 and DE-A 10046672. Multimetal oxide compositions having a chemical composition like that of the oxide compositions of the formula (I) are also known from WO 00/29106.

The use of multimetal oxide compositions having such a catalyst composition for the heterogeneously catalyzed gas-phase oxidation of propane to acrylic acid has already been proposed in the above-cited prior art.

Acrylic acid is an important ethylenically unsaturated compound which is used both as such and also in the form of its alkyl esters for preparing polymers.

An aspect common to all publications of the above-cited prior art is that they use the multimetal oxide compositions of the formula (I) in crushed form for the catalysis of the gas-phase oxidation of propane to acrylic acid.

Although this gives the catalyst charge an increased activity, which is advantageous in the case of the relatively unreacted propane, the significantly more valuable catalyst property, namely the selectivity of acrylic acid formation, is not fully satisfactory when crushed multimetal oxide compositions are used.

DE-A 4442346 relates to a process for producing coated catalysts comprising multimetal oxide compositions similar to those of the formula (I).

DE-A 4442346 recommends these coated catalysts as catalysts for the gas-phase catalytic oxidation of acrolein to acrylic acid.

EP-A 1090684 is also relevant prior art.

SUMMARY OF THE INVENTION

It is an object of the present invention to provide the multimetal oxide compositions (I) in a form other than crushed material which, when used as catalysts for the gas-phase catalytic oxidation of propane to acrylic acid, gives increased selectivity of acrylic acid formation.

BRIEF DESCRIPTION OF THE DRAWINGS

FIG. 2 shows the associated X-ray diffraction pattern of the comparative example.

DETAILED DESCRIPTION OF THE INVENTION

Figure 1:
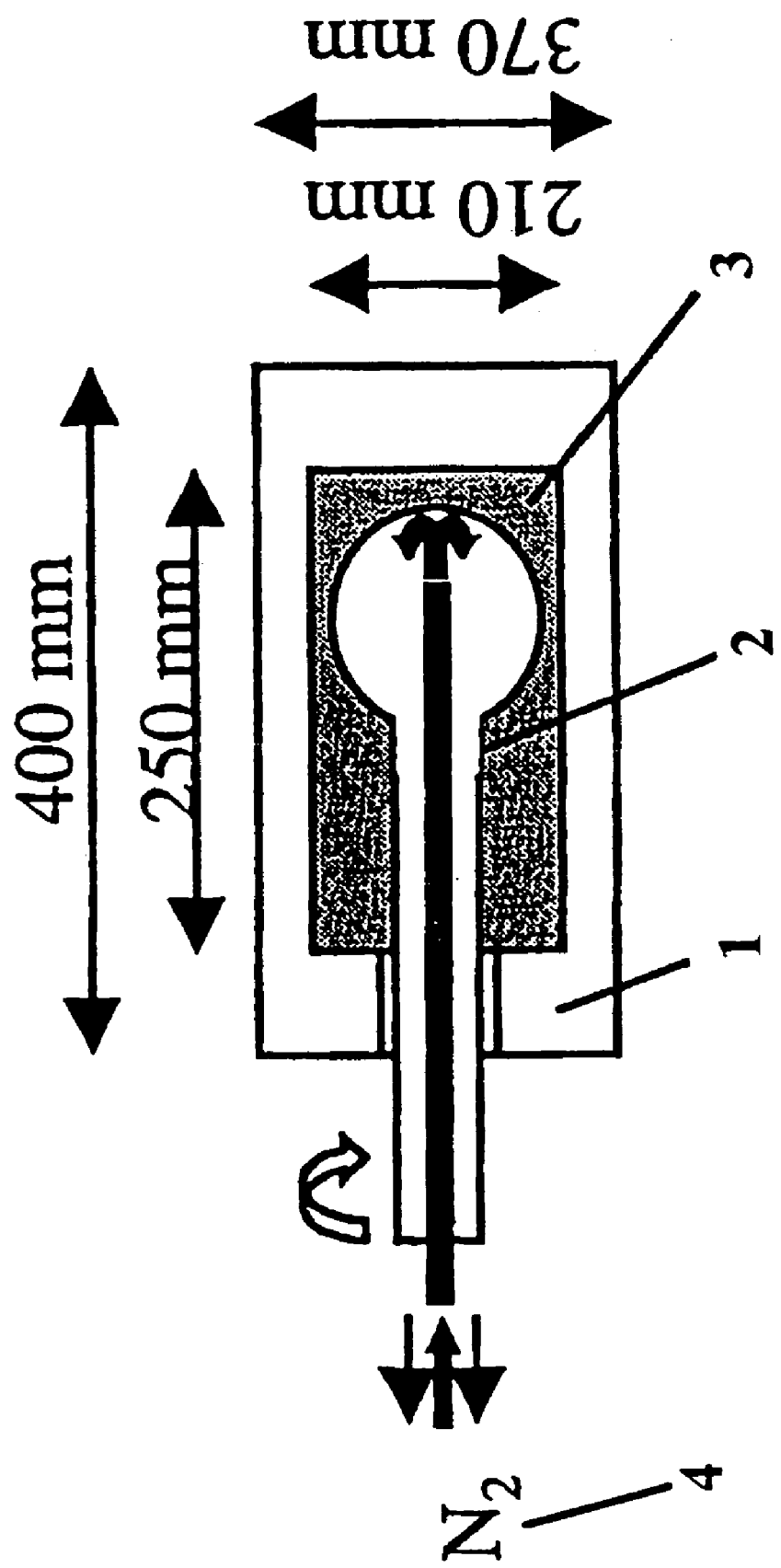
FIG. 1 shows a rotary bulb furnace (1=furnace housing, 2=rotary bulb, 3=heated chamber, 4=nitrogen/air stream).

We have found that this object is achieved by a catalyst comprising a support body and a catalytically active oxide composition of the formula I $$Mo_1V_bM_c^1M_d^2O_n \qquad (I),$$

where
 $M^1$=Te and/or Sb,
 $M^2$=at least one element selected from the group consisting of Nb, Ta, W, Ti, Al, Zr, Cr, Mn, Ga, Fe, Ru, Co, Rh, Ni, Pd, Pt, Bi, B and Ce,
 b=0.01 to 1,
 c=0.01 to 1,
 d=0.01 to 1 and
 n=a number required to achieve electrical neutrality and determined by the valence and abundance of the elements other than oxygen in (I), applied to the surface of the support body.

According to the present invention, preference is given to using oxide compositions of the formula (I) in which $M^1$=Te. Furthermore, it is favorable according to the present invention for $M^2$ to be Nb, Ta, W and/or titanium. $M^2$ is preferably Nb.

The stoichiometric coefficient b of the oxide compositions of the formula (I) to be used according to the present invention is advantageously from 0.1 to 0.6. Correspondingly, the preferred range for the stoichiometric coefficient c is from 0.05 to 0.4 and favorable values for d are in the range from 0.1 to 0.6. Particularly useful oxide compositions of the formula (I) to be used according to the present invention are those in which the stoichiometric coefficients b, c and d are simultaneously in the abovementioned preferred ranges.

Further stoichiometries which are suitable according to the present invention for the oxide compositions of the formula (I) to be used according to the present invention are those disclosed in the publications of the above-cited prior art, in particular the publications EP-A 608838, WO 00-29106, JP-A 11/169716 and EP-A 962253.

The support bodies to be used according to the present invention are preferably chemically inert, i.e. they do not play a significant role in the reaction occurring in the catalytic gas-phase oxidation of propane to acrylic acid which is catalyzed by the coated catalysts of the present invention. According to the present invention, possible materials for the support bodies are, in particular, aluminum oxide, silicon dioxide, silicates such as clay, kaolin, steatite, pumice, aluminum silicate and magnesium silicate, silicon carbide, titanium dioxide and thorium dioxide.

The surface of the support body can be either smooth or rough. The surface of the support body is advantageously rough, since an increased surface roughness generally results in increased adhesion of the applied shell of active composition.

The surface roughness $R_z$ of the support body is frequently in the range from 5 to 200 mm, often in the range from 20 to 100 mm (determined in accordance with DIN 4768 part 1 by means of a "Hommel Tester" for DIN-ISO surface area measurements from Hommelwerke, Germany).

Furthermore, the support material may be porous or nonporous. The support material is advantageously nonporous (total volume of the pores $\leq 1\%$ of the volume of the support body).

The thickness of the active oxide composition layer present on the coated catalysts of the present invention is usually from 10 to 1000 μm, however, it can also be from 100 to 700 μm, from 200 to 600 μm or from 300 to 500 μm. Further possible coating thicknesses are from 10 to 500 μm, from 100 to 500 μm or from 200 to 300 μm.

In principle, any geometries of the support bodies are suitable for the process of the present invention. Their longitudinal dimension is generally from 1 to 10 mm. However, preference is given to using spheres or cylinders, in particular hollow cylinders, as support bodies. Useful diameters of support spheres are from 1.5 to 4 mm. If cylinders are used as support bodies, their length is preferably from 2 to 10 mm and their external diameter is preferably from 4 to 10 mm. In the case of rings, the wall thickness is usually from 1 to 4 mm. Ring-shaped support bodies suitable for the purposes of the present invention can also have a length of from 3 to 6 mm, an external diameter of from 4 to 8 mm and a wall thickness of from 1 to 2 mm. However, a support ring geometry of 7 mm×3 mm×4 mm or 5 mm×3 mm×2 mm (external diameter×length×internal diameter) is also possible.

The simplest way of producing the coated catalysts of the present invention is to preform active oxide compositions of the formula (I), convert them into a finely divided form and finally apply them to the surface of the support body with the aid of a liquid binder. For this purpose, the surface of the support body is most simply moistened with the liquid binder and a layer of the active composition is applied to the moistened surface by bringing it into contact with finely divided active oxide composition of the formula (I). Finally, the coated support body is dried. It is of course also possible to repeat the procedure periodically in order to achieve an increased coating thickness. In this case, the coated base body becomes the new "support body", etc.

The fineness of the catalytically active oxide composition of the formula (I) to be applied to the surface of the support body is of course matched to the desired thickness of the coating. For coating thicknesses in the range from 100 to 500 mm, suitable active composition powders are, for example, powders of which at least 50% of the total number of powder particles pass a sieve having a mesh opening of from 1 to 20 μm and whose proportion by number of particles having a longitudinal dimension above 50 μm is less than 10%. In general, the distribution of the longitudinal dimensions of the powder particles corresponds to a Gauss distribution as a result of the method of manufacture.

To carry out the coating process described on an industrial scale, it is useful to employ, for example, the process principle disclosed in DE-A 2909671. In this, the support bodies to be coated are placed in a preferably inclined (the angle of inclination is generally $\geq 0°$ and $\leq 90°$, usually $\leq 30°$ and $\geq 90°$; the angle of inclination is the angle of the axis of the rotary vessel relative to the horizontal) rotating vessel (e.g. rotary pan or coating drum). The rotating vessel conveys the, for example, spherical or cylindrical support bodies under two successive metering devices located a particular distance apart. The first of the two metering devices advantageously corresponds to a nozzle (e.g. an atomizer nozzle operated by means of compressed air) by means of which the support bodies rolling in the rotating vessel are sprayed with the liquid binder and moistened in a controlled manner. The second metering device is located outside the atomization cone of the liquid binder sprayed in and serves to introduce the finely divided oxidic active composition (e.g. via a vibratory chute or powder screw). The support spheres which have been moistened in a controlled manner take up the introduced active composition powder which is compacted on the outer surface of the, for example, cylindrical or spherical support body by the rolling motion to give a coherent coating.

If necessary, the support body which has been initially coated in this way once again passes under the spray nozzle during the subsequent revolution, is moistened in a controlled manner so that it can take up a further layer of finely divided oxidic active composition as it moves along further, and so forth (intermediate drying is generally not necessary). Finely divided oxidic active composition and liquid binder are generally fed in continuously and simultaneously.

After coating has been completed, the liquid binder can be removed, for example, by action of hot gases such as $N_2$ or air. It is notable that the coating process described gives not only fully satisfactory adhesion of the successive layers to one another but also of the initial layer to the surface of the support body.

For the coating method described above, it is important that the moistening of the surface to be coated of the support body is carried out in a controlled manner. Expressed briefly, this means that the support surface is advantageously moistened so that although this has water absorbed on it, no liquid phase can be observed visually on the support surface. If the support body surface is too moist, the finely divided catalytically active oxide composition agglomerates to form separate agglomerates instead of adhering to the surface. Details may be found in DE-A 2909671.

The abovementioned final removal of the liquid binder used can be carried out in a controlled manner, e.g. by vaporization and/or sublimation. In the simplest case, this can be achieved by action of hot gases having an appropriate temperature (frequently from 50 to 300° C., often 150° C.). However, it is also possible for only predrying to be carried out by action of hot gases. Final drying can then, for example, be carried out in a drying oven of any type (e.g. belt dryer) or in the reactor. The temperature employed should not be above the calcination temperature used for the preparation of the oxidic active composition. Of course, drying can also be carried out purely in a drying oven.

As binders in the coating process, it is possible to use, regardless of the type and geometry of the support body: water, monohydric alcohols such as ethanol, methanol, propanol and butanol, polyhydric alcohols such as ethylene glycol, 1,4-butanediol, 1,6-hexanediol or glycerol, monobasic or polybasic organic carboxylic acids such as propionic acid, oxalic acid, malonic acid, glutaric acid or maleic acid, amino alcohols such as ethanolamine or diethanolamine and also monofunctional or polyfunctional organic amides such as formamide. Useful binders also include solutions comprising from 20 to 90% by weight of water and from 10 to 80% by weight of an organic compound which has a boiling point or sublimation temperature at atmospheric pressure (1 atm) >100° C., preferably >150° C., and is dissolved in the water. The organic compound is advantageously selected from the above listing of possible organic binders. The proportion of the organic components in the abovementioned aqueous binder solutions is preferably from 10 to 50% by weight and particularly preferably from 20 to 30% by weight. Suitable organic components also include monosaccharides and oligosaccharides such as glucose, fructose, sucrose or lactose and also polyethylene oxides and polyacrylates.

The preparation of catalytically active oxide compositions of the formula (I) can be carried out in a manner known per se as described in the above-cited publications of the prior art, i.e. the preparation can be carried out, for example both hydrothermally as descried, for example, in DE-A 10033121 and by conventional means.

In the latter case, the catalytically active oxide compositions of the formula (I) are obtainable by producing a very intimate, preferably finely divided dry mixture of suitable sources of the elemental constituents of the oxide compositions and treating this mixture thermally at from 350 to 700° C. or from 400 to 650° C. or from 400 to 600° C. The thermal treatment can be carried out under an oxidizing atmosphere, a reducing atmosphere or an inert atmosphere. A suitable oxidizing atmosphere is, for example, air, air enriched with molecular oxygen or air depleted in molecular oxygen. The thermal treatment is preferably carried out under an inert atmosphere, i.e., for example, under molecular nitrogen and/or noble gas. The thermal treatment is preferably carried out at atmospheric pressure (1 atm). Of course, the thermal treatment can also be carried out under reduced pressure or under slightly superatmospheric pressure.

If the thermal treatment is carried out under a gaseous atmosphere, this can be either stationary or flowing. The thermal treatment can take a total time of up to 24 hours or more.

The thermal treatment is preferably carried out initially under an oxidizing (oxygen-containing) atmosphere (e.g. in air) at from 150 to 400° C. or from 250 to 350°C. The thermal treatment is then advantageously continued under inert gas (e.g. molecular nitrogen) at from 350 to 700° C. or from 400 to 650° C. or from 400 to 600° C. Of course, the thermal treatment can also be carried out such that the catalyst precursor composition is initially, i.e. before thermal treatment, tabletted (if appropriate after pulverization and with or without addition of from 0.5 to 2% by weight of finely divided graphite), then treated thermally and subsequently comminuted again.

For the purposes of preparing catalytically active oxide compositions of the formula (I), the starting compounds can be intimately mixed in dry or wet form. If the starting compounds are mixed dry, they are advantageously used as finely divided powders and after mixing and optionally compaction are subjected to calcination (thermal treatment).

However, the intimate mixing is preferably carried out wet. Here, the starting compounds are usually mixed with one another in the form of an aqueous solution and/or suspension. This aqueous composition is subsequently dried and then calcined. The aqueous composition is advantageously an aqueous solution. Drying is preferably carried out immediately after preparation of the aqueous mixture and by spray drying (the outlet temperatures are generally from 100 to 150° C. and the inlet temperatures are frequently from 220 to 340° C.; spray drying can be carried out in cocurrent or in countercurrent), which gives a particularly intimate dry mixture, especially when the aqueous composition to be spray dried is an aqueous solution.

For the purposes of the above-described method of preparing the catalytically active oxide compositions of the formula (I), suitable sources of the elemental constituents are all those which are able to form oxides and/or hydroxides on heating (if necessary in air). It is of course also possible to use, in part or exclusively, oxides and/or hydroxides of the elemental constituents as starting compounds.

Sources of the element Mo which are suitable for the purposes of the present invention are, for example, molybdenum oxides such as molybdenum trioxide, molybdates such as ammonium heptamolybdates tetrahydrate and molybdenum halides such as molybdenum chloride.

Suitable starting compounds for the element V which can be used according to the present invention are, for example, vanadyl acetylacetonate, vanadates such as ammonium metavanadate, vanadium oxides such as vanadium pentoxide ($V_2O_5$), vanadium halides such as vanadium tetrachloride ($VCl_4$) and vanadium oxyhalides such as $VOCl_3$. It is also possible to use vanadium starting compounds in which the vanadium is present in the oxidation state +4.

According to the present invention, suitable sources of the element tellurium are tellurium oxides such as tellurium dioxide, metallic tellurium, tellurium halides such as $TeCl_2$, and also telluric acids such as orthotelluric acid $H_6TeO_6$.

Advantageous starting compounds of antimony are antimony halides such as $SbCl_3$, antimony oxides such as antimony trioxide ($Sb_2O_3$), antimonic acids such as HSb$(OH)_6$, and also antimony oxide salts such as antimony oxide sulfate $(SbO_2)SO_4$.

Niobium sources which are suitable for the purposes of the present invention are, for example, niobium oxides such as niobium pentoxide ($Nb_2O_5$), niobium oxide halides such as $NbOCl_3$, niobium halides such as $NbCl_5$, and also complexes of niobium and organic monocarboxylic acids and/or polycarboxylic acids such as citrates, oxalates, and also niobium alkoxides. Of course, the Nb-containing solutions used in EP-A 895 809 are also suitable as niobium source.

With regard to all other possible elements $M^2$, starting compounds which are particularly suitable for the purposes of the present invention are their halides, nitrates, formates, oxalates, acetates, citrates, carbonates and/or hydroxides. Suitable starting compounds are frequently also their oxo compounds such as tungstates or the acids derived from these. Ammonium salts are also frequently used as starting compounds.

Further starting compounds which can be used for preparing the catalytically active oxide compositions of the formula (I) of the present invention are polyanions of the Anderson type, as described, for example, in JP-A 2000-143244 and in Polyhedron Vol. 6, No. 2, pp. 213–218, 1987. A further suitable literature source for polyanions of the Anderson type is Kinetics and Catalysis, Vol. 40, No. 3, 1999, pp. 401 to 404.

Other polyanions suitable as starting compounds are, for example, those of the Dawson or Keggin type. According to the present invention, preference is given to using starting compounds which are converted into their oxides at elevated temperatures, either in the presence or in the absence of oxygen, with liberation of gaseous compounds.

According to the present invention, preference is given to coated catalysts whose catalytically active composition of the formula (I) has an X-ray diffraction pattern (Cu-K$_a$ radiation) which displays reflections h, i and optionally k whose maxima are at 2Θ values of 22.2±0.4° (h), 27.3±0.4° (i) and 28.2±0.4° (k).

It is advantageous according to the present invention for the reflection h to be the most intense reflection in the X-ray diffraction pattern.

It is also advantageous according to the present invention for the reflection h to have a width at half height of not more than 0.5°.

The definition employed in the present text for the intensity of a reflection in the X-ray diffraction pattern is based on the definition given in DE-A 19835247.

According to this definition, if A$^1$ denotes the apex (maximum) of a reflection 1 and B$^1$ denotes the nearest pronounced minimum (minima in the form of shoulders on the reflection are not taken into account) in the direction of the intensity axis perpendicular to the 2Θ to the left of the apex A$^1$ and B$^2$ correspondingly denotes the nearest pronounced minimum to the right of the apex A$^1$ and C$^1$ denotes the point at which a straight line drawn perpendicularly to the 2Θ axis from the apex A$^1$ intersects a straight line connecting the points B$^1$ and B$^2$, then the intensity of the reflection 1 is the length of the straight line A$^1$C$^1$ extended from the apex A$^1$ to the point C$^1$. The expression minimum here refers to a point at which the gradient of a tangent to the curve in the base region of the reflection 1 changes from a negative value to a positive value, or a point at which the gradient tends to zero, with the coordinates of the 2Θ axis and the intensity axis being employed for determining the gradient.

The width at half height is, for the purposes of the present text, correspondingly the length of the straight line between the two intersections H$^1$ and H$^2$ when a parallel to the 2Θ axis is drawn through the mid point of the straight line A$^1$C$^1$, where H$^1$ and H$^2$ are the first intersections to the left and right, respectively, of A$^1$ of this parallel with the above-defined line of the X-ray diffractogram.

The determination of the width at half height and the intensity is also shown by way of example in FIG. 6 of DE-A 10046672.

Furthermore, it is preferred that the intensity P$_i$ of the reflection i and the intensity P$_k$ of the reflection k obey the relationship 0.2≦R≦1 (preferably 0.5≦R≦1 and particularly preferably 0.8≦R≦1), where R is the intensity ratio defined by the formula $$R=P_i/(P_i+P_k).$$

It is also advantageous for the width at half height of the reflection i and any reflection k present to be ≦1° in each case.

It is particularly advantageous for the X-ray diffraction pattern to meet the abovementioned boundary conditions simultaneously.

Apart from the reflections h, i and optionally k, the X-ray diffraction pattern of advantageous catalytically active oxide compositions of the formula (I) contains further reflections whose maxima are at the following 2Θ values:

9.0±0.4° (l), 29.2±0.4° (m)

and 35.4±0.4° (n)

It is advantageous for the X-ray diffraction pattern of the catalytically active oxide compositions of the formula (I) to display additional reflections whose maxima are at the following 2Θ values:

6.7±0.4° (o), 7.9±0.40° (p), and 45.2±0.4° (q).

If the X-ray diffraction pattern of the catalytically active oxide composition of the formula (I) contains the reflection k, it generally displays further reflections whose maxima are at the following 2Θ values:

36.2±0.4° and 50.0±0.4°.

If the reflection h is assigned the intensity 100, it is advantageous for the reflections i, l, m, n, o, p, q to have, on the same intensity scale, the following intensities:

i: from 5 to 95, frequently from 5 to 80, sometimes from 10 to 60;
l: from 1 to 30;
m: from 1 to 40;
n: from 1 to 40;
o: from 1 to 30;
p: from 1 to 30 and
q: from 5 to 60.

If the X-ray diffraction pattern contains any of the abovementioned additional reflections, the width at half height of these is generally ≦1°.

All the figures in the present text relating to an X-ray diffraction pattern are based on an X-ray diffraction pattern produced using Cu-Ka radiation (Siemens diffractometer Theta-Theta D-5000, tube volume: 40 kV, tube current: 40 mA, aperture V20 (variable), collimator V20 (variable), secondary monochromator aperture (0.1 mm), detector aperture (0.6 mm), measurement interval (2Θ): 0.02%, measurement time per step: 2.4 s, detector: scintillation counter).

However, it is an important aspect of the present invention that the active oxide compositions of the formula (I) from WO 00-29106 which have an essentially amorphous structure indicated in the X-ray diffraction pattern by very broad reflections having maxima at 2Θ values of about 22° and about 27° are also suitable for producing the coated catalysts of the present invention.

Further suitable active oxide compositions of the formula (I) are those described in EP-A 529853 and EP-A 608838, which display very narrow reflections with maxima at 2Θ values of 22.1±0.3°, 28.2±0.3°, 36.2±0.3°, 45.2±0.3° and 50.0±0.3°.

Another important aspect of the present invention is that the coated catalysts of the present invention can be produced not only by application of the finished, finely milled active oxide compositions of the formula (I) to the moistened support body surface.

Instead, it is possible to apply not the active oxide composition itself but rather a finely divided precursor composition of this to the moistened support surface (using the same coating process and binder) and carrying out calcination after drying the coated support body.

As such a finely divided precursor composition, it is possible to use, for example, a composition obtainable by firstly producing a very intimate, preferably finely divided, dry mixture from the sources of the elemental constituents of the desired active oxide composition of the formula (I) (e.g. by spray drying an aqueous suspension or solution of the sources) and treating this finely divided dry mixture thermally (if desired after tableting with addition of from 0.5 to 2% by weight of finely divided graphite) at from 150 to 350° C., preferably from 250 to 350° C., under an oxidizing (oxygen-containing) atmosphere (e.g. in air) (for a few hours) and finally subjecting the material to milling if necessary.

After the support bodies have been coated with the precursor composition, they are calcined at from 360 to 700° C. or from 400 to 650° C. or from 400 to 600° C., preferably under an inert gas atmosphere (all other atmospheres are also possible).

Otherwise, the coated catalysts of the present invention can be used as catalysts for the gas-phase catalytical oxidation of propane to acrylic acid essentially as described in EP-A 962253, EP-A 608838, WO 00/29106 and JP-A 10-36311.

For example, the reaction gas mixture which is passed over the bed of the coated catalysts of the present invention at reaction temperatures of from 200 to 550° C. or from 230 to 480° C. or from 300 to 440° C. can have the following composition:
from 1 to 15, preferably from 1 to 7, % by volume of propane,
from 44 to 99% by volume of air and
from 0 to 55% by volume of water vapor.

To achieve a very high selectivity of acrylic acid formation, preference is given to reaction gas starting mixtures in which water vapor is present.

Further possible compositions of the reaction gas starting mixture are:
from 70 to 95% by volume of propane,
from 5 to 30% by volume of molecular oxygen and
from 0 to 25% by volume of water vapor.

The heterogeneously catalyzed gas-phase oxidation of propane to acrylic acid using the coated catalysts of the present invention can be carried out in a manner known per se in shell-and-tube reactors cooled by means of a salt bath, as are known for the heterogeneously catalyzed gas-phase oxidation of propene to acrolein or of acrolein to acrylic acid and are described, for example, in EP-A 700714, in EP-A 700893 and in the prior art cited in these two publications. Reaction gas mixture and salt bath can be passed through the reactor either in cocurrent or in countercurrent. A crossflow can additionally be superposed on the salt bath. If necessary, the salt bath can be passed around the catalyst-containing tubes in a meandering manner.

Of course, the process of the present invention gives a product gas mixture which does not consist exclusively of acrylic acid. Rather, the product gas mixture further comprises unreacted propane together with secondary components such as propene, acrolein, $CO_2$, CO, $H_2O$, acetic acid, propionic acid, etc., from which the acrylic acid has to be separated.

This can be carried out in the manner known from the heterogeneously catalyzed gas-phase oxidation of propene to acrylic acid.

For example, the acrylic acid present in the product gas mixture can be absorbed in water or absorbed in a high-boiling inert hydrophobic organic solvent (e.g. a mixture of diphenyl ether and Diphyl which may further comprise additives such as dimethyl phthalate). The resulting mixture of absorption medium and acrylic acid can subsequently be worked up in a manner known per se by rectification, extraction and/or crystallization to give pure acrylic acid. As an alternative, the basic separation of the acrylic acid from the product gas mixture can be carried out by fractional condensation as described, for example, in DE-A 19 924 532.

The resulting aqueous acrylic acid condensate can then be purified further by, for example, fractional crystallization (e.g. suspension crystallization and/or layer crystallization).

The residual gas mixture remaining after the basic separation of the acrylic acid comprises, in particular, unreacted propane. This can be separated from the residual gas mixture by, for example, fractional pressure rectification and subsequently be returned to the gas-phase oxidation according to the present invention. However, it is more advantageous to bring the residual gas into contact with a hydrophobic organic solvent capable of preferentially absorbing the propane in an extraction apparatus (e.g. by passing the gas through the solvent).

Subsequent desorption and/or stripping with air enables the absorbed propane to be set free again and be returned to the process of the present invention. Economical total propane conversions can be achieved in this way.

It is an important aspect of the present invention that the coated catalysts of the present invention give a higher selectivity of acrylic acid formation than do crushed active oxide compositions of the formula I.

The coated catalysts of the present invention are also suitable for the preparation of methacrylic acid by gas-phase catalytic oxidation of $C_4$ precursors such as n-butane, isobutane or isobutene and for the preparation of acrylic acid by gas-phase catalytic oxidation of propene. Finally, it may be stated that coated catalysts of the present invention which have become exhausted in a gas-phase catalytic propane oxidation to form acrylic acid or butane oxidation to form methacrylic acid can be regenerated as described in EP-A 339119.

COMPARATIVE EXAMPLE AND EXAMPLE

Comparative Example 1287.25 g of ammonium metavanadate (77.5% by weight of $V_2O_5$, from G.f.E. Nuremberg, Germany) were dissolved at 80° C. while stirring in a stainless steel vessel. This gave a clear, yellowish solution. This solution was cooled to 60° C. and, while maintaining the temperature of 60° C., 1683.75 of telluric acid (99% by weight of $H_6TeO_6$, from Fluka, Germany) and 5868.0 g of ammonium heptamolybdate (81.5% by weight of $MoO_3$, from Starck, Germany) were then stirred into the solution in succession in the order indicated. This gave a deep red solution A.

In a second heatable vessel made of stainless steel, 1599 g of ammonium niobium oxalate 21.1% by weight of Nb, from Starck, Germany) were dissolved in 8.3 l of water while stirring at 60° C. (solution B).

The solution A and the solution B were cooled to 30° C. and combined at this temperature while stirring, with the solution B being added to the solution A. The addition was carried out continuously over a period of 10 minutes. This gave an orange suspension.

This suspension was subsequently spray dried in a spray dryer from Niro (Niro A/S Atomizer, Transportable Minor spray drier, centrifugal atomizer from Niro, Denmark). The temperature of the feed was 30° C. The gas inlet temperature $T^{in}$ was 240° C. and the gas outlet temperature $T^{out}$ was 110° C. The resulting spray-dried powder was likewise orange.

1% by weight of graphite was added to the spray-dried powder and the mixture was pressed to form annular tablets having dimensions of 16 mm×2.5 mm×8 mm (external diameter×height×internal diameter) (the pressure applied was 50 MPa, and the resulting lateral compressive strength was 10 N).

100 g of these rings were calcined in a rotary bulb furnace as shown in FIG. 1 (1=furnace housing, 2=rotary bulb, 3=heated chamber, 4=nitrogen/air stream) by firstly heating them linearly from 25° C. to 275° C. over a period of 27.5 minutes under an air stream of 50 standard l/h. This temperature was subsequently maintained for 1 hour while also maintaining the air flow.

The air stream was then replaced by a nitrogen stream of 50 standard l/h and the calcination temperature was increased linearly from 275° C. to 600° C. over a period of 32.5 minutes. This temperature was then maintained for 2 hours and the entire rotary bulb furnace was subsequently allowed to cool by itself to room temperature.

Black tablets having the composition $Mo_{1.0}$ $V_{0.33}$ $Te_{0.15}$ $Nb_{0.11}$ $O_x$ (stoichiometry of amounts weighed out: $Mo_{1.0}$ $V_{0.33}$ $Te_{0.22}$ $Nb_{0.11}$ $O_x$) were obtained.

The associated X-ray diffraction pattern is shown in FIG. 2.

The resulting tablets of oxidic active compositions were crushed in a mortar and the particle fraction which passes a square sieve mesh having an edge length of 1.2 mm but is retained by a square sieve mesh having an edge length of 0.6 mm was separated off by sieving.

A tube reactor made of steel (internal diameter: 8.5 mm, length: 140 cm, wall thickness: 2.5 cm) was charged with 7 g of the sieve fraction which had been separated off (catalyst bed length=11 cm). A preliminary bed of 30 cm of crushed quartz (particle size: 1–2 mm) was placed in the tube reactor before the bed of active oxide composition and a finishing bed of the same crushed quartz was placed in the remaining length of the tube reactor after the bed of active oxide composition.

The exterior wall temperature of the charged reaction tube was brought to 350° C. over its entire length by means of external electrically heated heating mats. A reaction gas starting mixture having the molar composition propane: air:$H_2O$=1:15:14 was then passed through the reaction tube (the inlet end was at the end of the finishing bed). The residence time (based on the bed of active composition) was set to 2.4 sec. The inlet pressure was 2 bar absolute.

After an operating time of 42 hours, the propane conversion after a single pass was 24 mol %. The selectivity of acrylic acid formation was 53 mol %. In addition, propene was formed as useful by-product with a selectivity of 10 mol %.

Example

The procedure of the comparative example was carried out twice to produce a double quantity of black annular tablets of oxidic active composition.

The annular tablets of oxidic active composition were milled dry in a Retsch mill to give a powder of which 50% of the powder particles passed a sieve having a mesh opening of from 1 to 20 mm and whose proportion by number of particles having a maximum dimension above 50 mm was less than 10%. 0.6 kg of steatite spheres (agglomerated crushed steatite, diameter: 2.5–3.2 mm, catalog no. 1.080023.60.00.00, surface roughness $R_z$=45 mm, total pore volume ≦1% of the volume of the support body, manufacturer: Hoechst Ceramtec, Germany) were placed in a coating vessel (angle of inclination: 45°; Hicoater from Lödige, Germany) having an internal volume of 3 l.

The coating vessel was then rotated at 16 rpm. 50 ml of a mixture of glycerol and water (weight ratio of glycerol: water=1:3) were sprayed via a nozzle onto the spherical support bodies over a period of 30 minutes. At the same time, 156 g of the powder obtained by milling the annular tablets was introduced continuously via a vibratory chute outside the spray cone of the atomizer nozzle. During the coating process, the powder introduced was all taken up by the surface of the support bodies. Agglomeration of the finely divided oxidic active composition was not observed. The coated support bodies were dried at 150° C. for 16 hours in a muffle furnace.

The resulting coated catalysts had a layer thickness of the active composition of 180 mm. This corresponded to an active composition content of the coated catalysts of 20% by weight.

A tube reactor made of steel (internal diameter: 8.5 mm, length: 1.40 cm, wall thickness: 2.5 cm) was charged with 35.0 g of the coated catalyst (catalyst bed length=55 cm). A preliminary bed of 30 cm of crushed quartz (particle size: 1–2 mm) was placed in the tube reactor before the bed of catalyst and a finishing bed of the same crushed quartz was placed in the remaining length of the tube reactor after the bed of catalyst.

The exterior wall temperature of the charged reaction tube was brought to 350° C. over its entire length by means of external electrically heated heating mats.

A reaction gas starting mixture having the molar composition propane:air:$H_2O$=1:15:14 was then passed through the reaction tube (the inlet end was at the end of the finishing bed). The residence time (based on the bed of active composition) was set to 2.4 sec. The inlet pressure was 2 bar absolute.

After an operating time of 42 hours, the propane conversion after a single pass was 25 mol %. The selectivity of acrylic acid formation was 58 mol %. In addition, propene was formed as useful by-product with a selectivity of 13 mol %.

We claim:

1. A process for the gas-phase catalytic oxidation of propane to acrylic acid comprising contacting a gaseous mixture comprising propane and oxygen with a catalyst to hetrogeneously catalyze the oxidation of propane to acrylic acid, wherein the catalyst used is a coated catalyst comprising a support body and a catalytically active oxide composition of the formula I

$$Mo_1V_bM_c^1M_d^2O_n \qquad (I),$$

where $M^1$=Te and/or Sb, $M^2$=at least one element selected from the group consisting of Nb, Ta, W, Ti, Al, Zr, Cr, Mn, Ga, Fe, Ru, Co, Rh, Ni, Pd, Pt, Bi, B and Ce, b=0.01 to 1, c=0.01 to 1, d=0.01 to 1 and n=a number required to achieve electrical neutrality and determined by the valence and abundance of the elements other than oxygen in (I), applied as a layer on the surface of the support body, wherein the longitudinal dimension of the support body is from 1 to 10 mm and the thickness of the active oxide composition layer present on the coated catalyst is from 10 to 700 μm.

2. The process as claimed in claim 1, wherein $M^1$=Te.

3. The process as claimed in claim 1, wherein $M^2$=Nb.

4. The process as claimed in claim 1, wherein b=0.1 to 0.6.

5. The process as claimed in claim 1, wherein c=0.05 to 0.4.

6. The process as claimed in claim 1, wherein d=0.1 to 0.6.

7. The process as claimed in claim 1, wherein the support body comprises aluminum oxide, silicon dioxide, clay, kaolin, steatite, pumice, aluminum silicate, magnesium silicate, silicon carbide, zirconium dioxide or thorium dioxide.

8. The process as claimed in claim 1, wherein the support body has a spherical or cylindrical geometry.

9. The process as claimed in claim 8, wherein the support body is a sphere having a diameter of from 1 to 10 mm.

10. The process as claimed in claim 8, wherein the support body is a ring having a length of from 2 to 10 mm, an external diameter of from 4 to 10 mm and a wall thickness of from 1 to 4 mm.

11. The process as claimed in claim 1, wherein the catalytically active oxide composition has an X-ray diffraction pattern which displays reflections h, i and optionally k whose maxima are at 2 Θ values of 22.2±0.4° (h), 27.3±0.4° (i) and 28.2±0.4° (k).

12. The process as claimed in claim 11, wherein the reflection h is the most intense reflection in the X-ray diffraction pattern.

13. The process as claimed in claim 11, wherein the reflection h has a width at half height of not more than 0.5°.

14. The process as claimed in claim 11, wherein the intensity $P_i$ of the reflection i and the intensity $P_k$ of the reflection k obey the relationship $0.2 \leq R \leq 1$, where R is the intensity ratio defined by the formula:

$$R=P_i/(P_i+P_k).$$

15. The process as claimed in claim 1, wherein the catalytically active oxide composition is applied in a layer thickness of from 200 to 600 μm to the surface of the support body.

* * * * *